US008044194B2

(12) United States Patent
Dubois et al.

(10) Patent No.: US 8,044,194 B2
(45) Date of Patent: Oct. 25, 2011

(54) CYCLIC CARBONYL MONOMERS FUNCTIONALIZED WITH CARBOHYDRATES, POLYMERS DERIVED THEREFROM, AND METHODS OF PREPARATION THEREOF

(75) Inventors: Philippe Dubois, Mons (BE); James L. Hedrick, San Jose, CA (US); Alshakim Nelson, San Jose, CA (US); Russell Pratt, Oakland, CA (US); Fabian Suriano, Mons (BE)

(73) Assignees: International Business Machines Corporation, Armonk, NY (US); The University of Mons-Hainaut (BE)

( * ) Notice: Subject to any disclaimer, the term of this patent is extended or adjusted under 35 U.S.C. 154(b) by 307 days.

(21) Appl. No.: 12/483,855

(22) Filed: Jun. 12, 2009

(65) Prior Publication Data

US 2010/0317838 A1 Dec. 16, 2010

(51) Int. Cl.
  *C07H 1/00* (2006.01)
  *C07H 3/00* (2006.01)
  *C08B 37/00* (2006.01)
(52) U.S. Cl. ......... 536/126; 536/4.1; 536/18.5; 536/124
(58) Field of Classification Search .................... None
  See application file for complete search history.

(56) References Cited

U.S. PATENT DOCUMENTS

| 4,586,755 | A | 5/1986 | Worbois |
| 5,861,107 | A | 1/1999 | Buysch et al. |
| 5,981,743 | A | 11/1999 | Gross et al. |
| 6,093,792 | A | 7/2000 | Gross et al. |
| 6,316,581 | B1 | 11/2001 | Gross et al. |
| 7,351,809 | B2 | 4/2008 | Ueno et al. |

FOREIGN PATENT DOCUMENTS

CN 1335330 A 2/2002

OTHER PUBLICATIONS

Hajime Komura et al., "Synehetic Studies by the Use of Carbonates. II. An Easy Method of Preparing Cyclic Carbonates of Polyhydroxy Compounds by Transesterification with Ethylene Carbonate," Bulletin of the Chemical Society of Japan, vol. 46, 550-553 (1973).
Xianhai Chen et al., "Versatile Copolymers from [L]-Lactide and [D]-Xylofuranose," Macromolecules 1999, 32, 308-314.
Youqing Shen et al., "Polycarbonates from Sugars: Ring-Opening Polymerization of 1,2-O-Isopropylidene-D-Xylofuranose-3,5-Cyclic Carbonate (IPXTC)," Macromolecules 1999, 32, 2799-2802.
Youqing Shen et al., "Aliphatic Polycarbonates with Controlled Quantities of D-Xylofuranose in the Main Chain," Macromolecules 1999, 32, 3891-3897.
Rajesh Kumar et al., "Functionalized Polyactides: Preparation and Characterization of [L]-Lactide-co-Pentofuranose," Macromolecules 2002, 35, 6835-6844.

M. Gracia Garcia-Martin et al., "Carbohydrate-Based Polycarbonates, Synthesis, Structure, and Biodegradation Studies," Macromolecules 2005, 38, 8664-8670.
Russell C. Pratt et al., "Exploration, Optimization, and Application of Supramolecular Thiourea-Amine Catalysts for the Synthesis of Lactide (Co)polymers," Macromolecules 2006, 39 (23), 7863-7871.
Russell C. Pratt et al., "Tagging Alcohols with Cyclic Carbonate: a Versatile Equivalent of (Meth)acrylate for Ring-Opening Polymerization," Chem. Commun., 2008, 114-116.
Hilbert M. Branderhorst et al., "Strong inhibition of cholera toxin binding by galactose dendrimers", Chem. Commun., 2007, pp. 5043-5045.
Henrik Ihre et al., "Fast and Convenient Divergent Synthesis of Aliphatic Ester Dendrimers by Anhydride Coupling", J. Am. Chem. Soc., 2001, vol. 123,. No. 25, pp. 5908-5917.
Mark L. Wolfenden et al., "Mannose/Glucose-Functionalized Dendrimers to Investigate the Predictable Tunability of Multivalent Interactions", J. Am. Chem. Soc., 2005, vol. 127, No. 35, pp. 12168-12169.
Eric K. Woller et al., "Altering the Strength of Lectin Binding Interactions and Controlling the Amount of Lectin Clustering Using Mannose/Hydroxyl-Functionalized Dendrimers", J. Am. Chem. Soc., 2003, vol. 125, No. 29, pp. 8820-8826.
Hans R. Kricheldorf et al., "Polymers of Carbonic Acid. XXVII. Macrocyclic Polymerization of Trimethylene Carbonate", Journal of Polymer Science: Part A: Polymer Chemistry, 1999, vol. 37, pp. 2179-2189.
Helmut Keul et al., "Anionic ring-opening polymerization of 2,2-dimethyltrimethylene carbonate", Makromol. Chem., 1986, 187, pp. 2579-2589.
Tetsuo Hino et al., "A Novel Synthetic Approach to Networked Polymers without Volume Shrinkage on Cross-Linking Polymerization: Cationic Copolymerization of a Monofunctional Epoxide and a Spiro Orthocarbonate Bearing Norbornene Backbone", Macromolecules, 2003, vol. 36, No. 16, pp. 5902-5904.

(Continued)

*Primary Examiner* — Patrick Lewis
(74) *Attorney, Agent, or Firm* — Cantor Colburn LLP

(57) ABSTRACT

A cyclic carbonyl monomer has the formula (7):

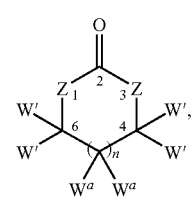

(7)

wherein at least one W' or $W^a$ group comprises a protected glycoside; each Z independently represents O, S, NH or NW"'; n is an integer from 0 to 6 wherein when n is 0, carbons labeled 4 and 6 are linked together by a single bond; each W' and $W^a$ group independently represents a hydrogen, a halide, an alkyl group comprising 1 to 20 carbons, an ester group comprising 1 to 20 carbons, an amide group, an aryl group comprising 1 to 20 carbons, an alkoxy group comprising 1 to 20 carbons, or a foregoing W' or $W^a$ group substituted with a protected glycoside; and each W"' group independently represents an alkyl group comprising 1 to 20 carbons, an aryl group comprising 1 to 20 carbons, or a foregoing W"' group substituted with a protected glycoside.

20 Claims, 2 Drawing Sheets

OTHER PUBLICATIONS

Michael Malkoch et al., "Rapid and Efficient Synthesis of Aliphatic Ester Dendrons and Dendrimers", Macromolecules, 2002, vol. 35, No. 22, pp. 8307-8314.

Karl D. Weilandt et al., "Synthesis and ring-opening polymerization of 2-acetoxymethyl-2-alkyltrimethylene carbonates and of 2-methoxycarbonyl-2-methyltrimethylen cearbonate; a comparison with the polymerization of 2,2-dimethyltrimethylene carbonate", Macromol. Chem. Phys., 1996, 197, pp. 3851-3868.

Eric K. Woller et al., "The Lectin-Binding Properties of Six Generations of Mannose-Functionalized Dendrimers", Organic Letters, 2002, vol. 4, No. 1, pp. 7-10.

G. Rokicki, "Aliphatic cyclic carbonates and spiroorthocarbonates as monomers", Prog. Polym. Sci. 25 (2000), pp. 259-342.

CYCLIC CARBONYL MONOMERS FUNCTIONALIZED WITH CARBOHYDRATES, POLYMERS DERIVED THEREFROM, AND METHODS OF PREPARATION THEREOF

BACKGROUND

The present invention relates to cyclic carbonyl monomers functionalized with carbohydrate moieties, ring opening polymers derived therefrom, and methods of preparation of the monomers and the polymers.

Biocompatible and biodegradable polymers that assemble into well-defined nanostructures such as micelles are of increasing interest as a means for drug transport and release. Moreover, polymers bearing pendant carbohydrates, specifically sugars, are particularly useful for applications that require the targeting of carbohydrate-binding proteins known as lectins. Protein-carbohydrate interactions mediate a number of biological processes, including cell growth, inflammation, infections and adhesion, via multivalent interactions. The enhancement in binding as a consequence of polyvalent interactions is known as the glycoside cluster effect. Carbohydrate-bearing polymers provide a platform for presenting multiple copies of a saccharide simultaneously, thus enhancing their affinity and selectivity for lectins.

A number of carbohydrate-bearing polymers have been developed including dendrimers, linear polymers, and micelles. Expanding the number of monomers useful in forming carbohydrate-bearing polymers is an ongoing need, directed toward achieving polymers having a wide range of tailorable solution, physical and mechanical properties.

BRIEF SUMMARY

Accordingly, the synthesis of new cyclic carbonate monomers comprising attached sugars has led to novel biocompatible and bioresorbable amphiphilic copolymers by ring-opening polymerization (ROP).

In one embodiment, a cyclic carbonyl monomer has the formula (7):

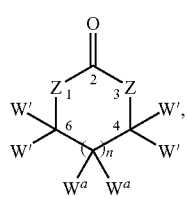

(7)

wherein at least one W' or W$^a$ group comprises a protected glycoside; each Z independently represents O, S, NH or NW'''; n is an integer from 0 to 6 wherein when n is 0, carbons labeled 4 and 6 are linked together by a single bond; each W' and W$^a$ group independently represents a hydrogen, a halide, an alkyl group comprising 1 to 20 carbons, an ester group comprising 1 to 20 carbons, an amide group, an aryl group comprising 1 to 20 carbons, an alkoxy group comprising 1 to 20 carbons, or a foregoing W' or W$^a$ group substituted with a protected glycoside; and each W''' group independently represents an alkyl group comprising 1 to 20 carbons, an aryl group comprising 1 to 20 carbons, or a foregoing W''' group substituted with a protected glycoside.

A method of preparing a cyclic carbonyl monomer comprising a protected glycoside comprises: preparing a first cyclic carbonyl monomer comprising a reactive carboxyl group selected from the group consisting of free carboxylic acid, acid chloride, and active ester; and esterifying the reactive carboxyl group of the first cyclic carbonyl monomer with a free hydroxyl group of a protected glycoside to produce the cyclic carbonyl monomer comprising the protected glycoside.

A polymer has the formula (9)

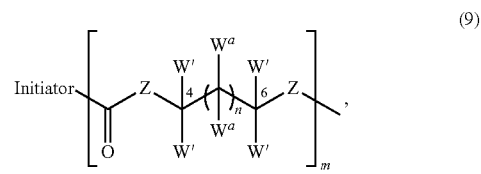

(9)

wherein at least one W' or W$^a$ group comprises a protected glycoside; m is an integer greater than 1; "Initiator" represents a polymerization initiator moiety; each Z independently represents O, S, NH or NW'''; n is an integer from 0 to 6, wherein when n is 0, carbons labeled 4 and 6 are linked together by a single bond; and each W' and W$^a$ group independently represents a hydrogen, a halide, an alkyl group comprising 1 to 20 carbons, an ester group comprising 1 to 20 carbons, an amide group, an aryl group comprising 1 to 20 carbons, an alkoxy group comprising 1 to 20 carbons, or a foregoing W' or W$^a$ group substituted with a protected glycoside; and each W''' group independently represents an alkyl group comprising 1 to 20 carbons, an aryl group comprising 1 to 20 carbons, or a foregoing W''' group substituted with a protected glycoside.

A method of ring opening polymerization comprises forming a reaction mixture comprising a cyclic carbonyl monomer comprising a protected glycoside, a catalyst, an initiator, and an optional solvent; and heating the reaction mixture to form a polymer comprising a protected glycoside.

For a better understanding of the advantages and features of the invention, refer to the following description and to the drawings.

DETAILED DESCRIPTION

Figure 1:
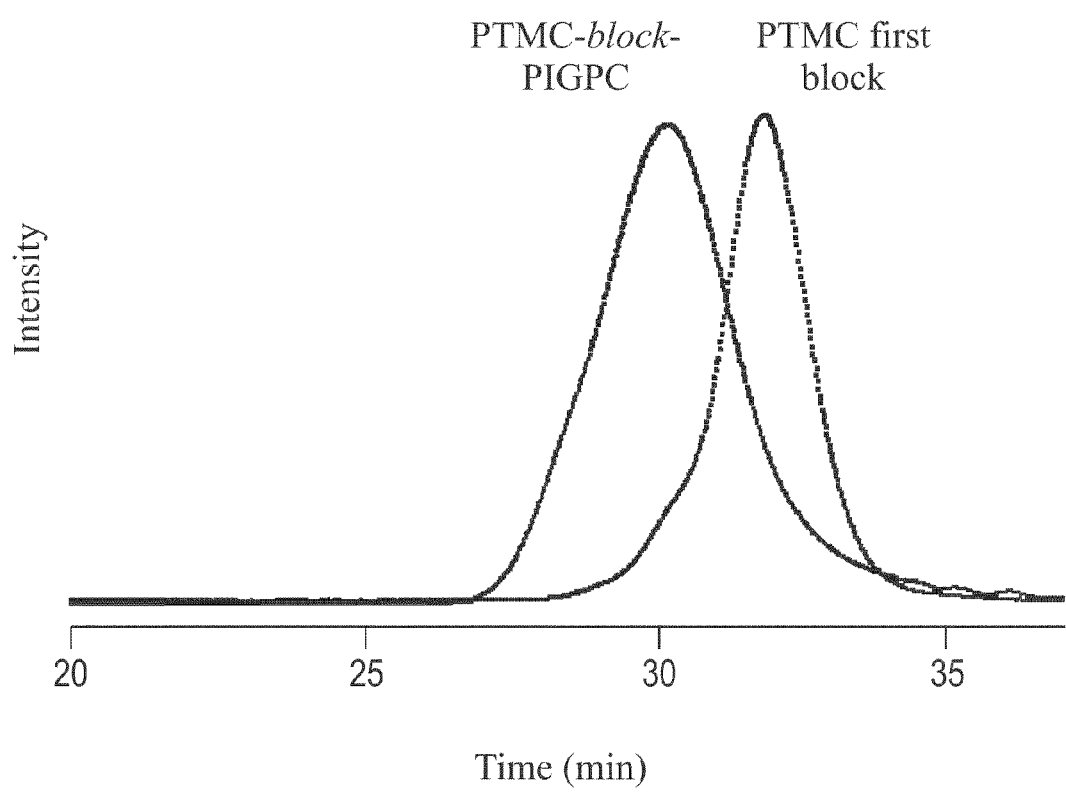
FIG. 1 is a gel permeation chromatogram (GPC) comparing PTMC-block-PIGPC copolymer to the homopolymer prepared from trimethylencarbonate, PTMC. PIGPC is the polymer formed from the cyclic carbonate monomer IGPC.

The homopolymers and block co-polymers described herein may be prepared via organo-catalyzed ring-opening polymerization (ROP) of new cyclic carbonate monomers comprising protected glycoside groups. A protected glycoside group is a protected sugar moiety or protected carbohydrate moiety. The polymers can comprise a pendant carbohydrate group, a carbohydrate group in the backbone, or a mixture thereof The polymers are biocompatible and biodegradable, and in some instances amphiphilic. An amphiphilic material is defined herein as a material that possesses some affinity for water and non-polar organic solvents, and has a hydrophilic (polar) portion that can be ionic or non-ionic and a hydrophobic (non-polar) portion. Examples of amphiphilic materials include surfactants such as sodium dodecyl sulfate and oleyl alcohol. The methods and materials disclosed herein provide monomers useful for adjusting polymer properties, including solubility, protein recognition and binding, biodegradability, viscoelastic properties, and micellization, among other physical and mechanical properties of interest.

Herein, a sugar is a monosaccharide, including aldohexoses, for example allose, altrose, glucose, mannose, gulose, idose, galactose, and talose; ketohexoses, for example fructose; aldopentoses, such as ribose and deoxyribose; and isomers of the foregoing compounds. Herein, a protected glycoside can be a compound or a chemical moiety containing a protected sugar. Generally, the protected glycoside is a cyclic structure derived from the hemiacetal or hemiketal form of the sugar. Particularly useful protecting groups for sugars include acetonides and other ketals. Other exemplary protecting groups include silyl ethers, benzyl ethers, t-butyl ethers, methoxymethyl ethers, and various esters.

Two methods are described for making cyclic carbonyl monomers containing a protected glycoside. In the first method, a protected glycoside having two free (i.e., unprotected) hydroxyl groups is treated with phosgene or a phosgene equivalent, such as triphosgene or another reactive carbonate, to form a cyclic carbonate monomer. In the second method, a pre-formed cyclic carbonyl monomer comprising a free carboxylic acid group or a reactive ester is treated with a protected glycoside having a free hydroxyl group to form an ester bearing the protected glycoside.

Generally, the cyclic carbonyl monomers are formed from precursor compounds comprising three or more carbons, two or more X groups, and optionally one or more carboxy groups (i.e., —COOH). The two or more X groups independently represent an alcohol, a primary amine, a secondary amine, or a thiol group. All of the cyclic carbonyl monomers disclosed herein are derived from precursor compounds having the general formula (3):

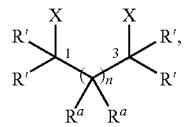

(3)

wherein each X independently represents OH, NHR", NH$_2$, or SH; n is an integer from 0 to 6, wherein when n is 0, carbons labeled 1 and 3 (attached to the X groups) are linked together by a single bond; each R' and R$^a$ group independently represents a hydrogen, a halide, a carboxy group, an alkyl group comprising 1 to 20 carbons, an ester group comprising 1 to 20 carbons, an amide group, an aryl group comprising 1 to 20 carbons, an alkoxy group comprising 1 to 20 carbons, or a foregoing R' or R$^a$ group substituted with a carboxy group; each R" group independently represents an alkyl group comprising 1 to 20 carbons, an aryl group comprising 1 to 20 carbons, or a foregoing R" group substituted with a carboxy group. The R', R$^a$ and R" groups can further independently comprise a cycloaliphatic ring, an aromatic ring, and/or a heteroatom such as oxygen, sulfur or nitrogen. The R', R$^a$ or R" groups can also together form a ring that can include a heteroatom such as oxygen, sulfur or nitrogen. In an embodiment, at least one of the R', R$^a$ or R" groups independently comprises a carboxy group, or a protected carboxy group such as an ester, amide or thioester. In another embodiment, n is 0 or 1, one R$^a$ group is methyl or ethyl, and the other R$^a$ group is a carboxy group.

Precursor compounds of formula (3) include protected glycosides having two free hydroxyl groups capable of forming a cyclic carbonate. An example is 1,2-O-isopropylidene-D-xylofuranose, IPXF, which when reacted with triphosgene, forms cyclic carbonate monomer, ICXF:

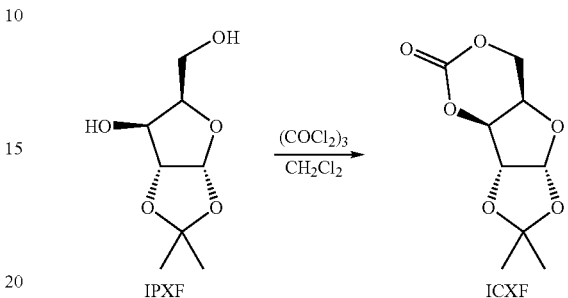

The isomeric purity is preserved in the reaction, as shown. In a ring-opening polymerization, ICXF forms a polycarbonate, PICXF, having the furanose ring in the backbone:

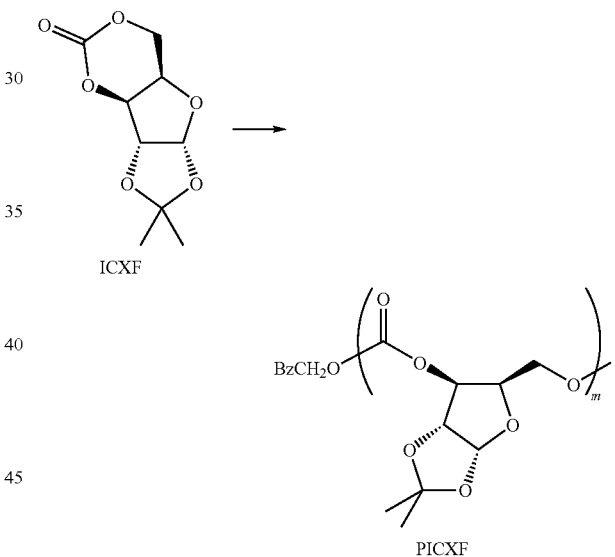

In this example, benzyl alcohol is the initiator and m has the same meaning described further below for formula (9). Other initiators can be used.

More specific precursor compounds of formula (3) have the general formula (4):

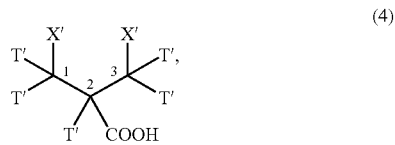

(4)

wherein each X' independently represents OH, NHT", NH$_2$, or SH; each T' can independently represent a hydrogen, a halide, a carboxy group (i.e., the moiety —COOH), an alkyl group comprising 1 to 20 carbons, an ester group comprising 1 to 20 carbons, an amide group, an aryl group comprising 1 to 20 carbons, an alkoxy group comprising 1 to 20 carbons, or a foregoing T' group substituted with a carboxy group; each T" independently represents an alkyl group comprising 1 to 20 carbons, an aryl group comprising 1 to 20 carbons, or a foregoing T" group substituted with a carboxy group. The T' and T" groups can further independently comprise a cycloaliphatic ring, an aromatic ring, or a heteroatom such as oxygen, sulfur or nitrogen. The T' or T" groups can also together form a ring that can include a heteroatom such as oxygen, sulfur or nitrogen. In an embodiment, none of the T' or T" groups comprises a carboxy group. In another embodiment, the T' attached to the carbon labeled 2 in formula (5) is an ethyl or methyl group, and all other T' groups are hydrogen.

A non-limiting example of a precursor compound of formula (4) is 2,2-bis(methylol)propionic acid, bis-MPA, which can be used to form various cyclic carbonyl monomers as shown in Scheme I:

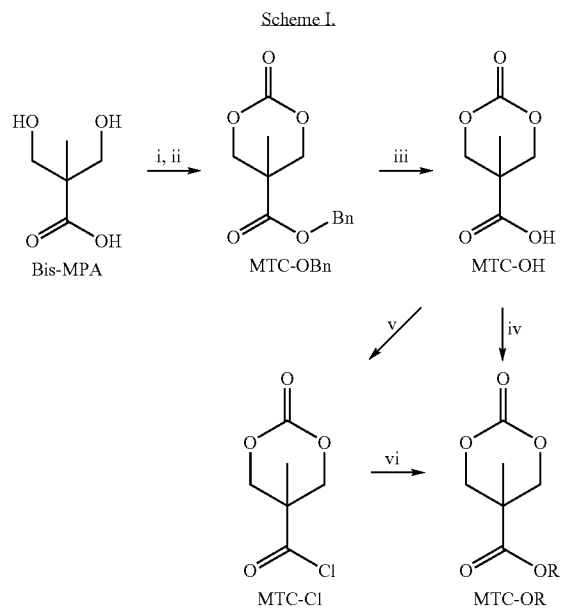

In Scheme 1, bis-MPA is first converted to a benzyl ester (i), followed by reaction of the alcohol groups with triphosgene (ii) to form a cyclic carbonyl monomer, MTC-OBn. MTC-OBn is then debenzylated (iii) to produce the cyclic carbonyl monomer, MTC-OH, as the free carboxylic acid. The carboxylic acid group of MTC-OH is then esterified with a protected glycoside, ROH, to form MTC-OR, where R is a protected glycoside moiety. Two pathways are shown for forming an ester with a protected glycoside having a free hydroxyl group. In the first pathway, (iv), the free acid, MTC-OH, is treated with a suitable carboxy activating agent, such as dicyclohexylcarbodiimide, DCC, which reacts with the protected glycoside to form MTC-OR in a single step. Alternatively, MTC-OH can be converted first (v) to an acid chloride, MTC-Cl, followed by treatment (vi) of MTC-Cl with ROH in the presence of a base to form MTC-OR. Both pathways are exemplary and are not meant to be limiting. The following conditions are typical for the reactions shown in Scheme 1: (i) Benzylbromide (BnBr), KOH, DMF, 100° C., 15 hours, 62% yield of the benzyl ester of bis-MPA. (ii) triphosgene, pyridine, $CH_2Cl_2$, −78° C. to 0C, 95% yield of MTC-OBn. (iii) Pd/C (10%), $H_2$ (3 atm), EtOAc, room temperature, 24 hours, 99% yield of MTC-OH. (iv) ROH, DCC, THF, room temperature, 1 to 24 hours. (v) $(COCl)_2$, THF, room temperature, 1 hour, 99% yield of MTC-Cl. (vi) ROH, $NEt_3$, RT, 3 hours yields MTC-OR.

The cyclic carbonyl monomer can comprise a cyclic carbonate, cyclic carbamate, cyclic urea, cyclic thiocarbonate, cyclic thiocarbamate, cyclic dithiocarbonate, or combinations thereof, derived from the two or more X groups. As shown above the cyclic carbonyl monomer can also comprise a non-sugar bearing ester group or a carboxylic acid, either of which can be converted to a protected glycoside bearing ester. It is understood that numerous synthetic pathways exist for forming esters from carboxylic acids and primary or secondary alcohols. Other numerous methods exist for preparing active esters that can be displaced by a primary or secondary alcohol to form an ester. The active ester can be formed before, after, or simultaneously with the formation of the cyclic carbonyl group. It is also understood that one method of linking the protected glycoside to the carboxy group might be more suitable than another due to steric constraints of the sugar, the propensity of the protected glycoside to racemize, relative hazards associated with the reagents, and other considerations effecting reaction efficiency, yield, and/or environmental impact.

The cyclic carbonyl monomers derived from the precursors of formula (3), of which MTC-OBn and MTC-OH in Scheme 1 are examples, have the general formula (5):

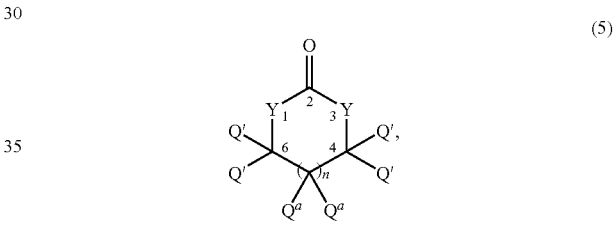

(5)

wherein at least one Q' or $Q^a$ group comprises a reactive carboxyl group selected the group consisting of carboxylic acid, acid chloride or active ester; each Y independently represents O, S, NH or NQ"; n is an integer from 0 to 6, wherein when n is 0, carbons labeled 4 and 6 (attached to each Y group) are linked together by a single bond; each Q' and $Q^a$ group independently represents a hydrogen, a halide, a carboxy group, an acid chloride group, an active ester, an alkyl group comprising 1 to 20 carbons, a non-active ester group comprising 1 to 20 carbons, an amide group, an aryl group comprising 1 to 20 carbons, an alkoxy group comprising 1 to 20 carbons, or a foregoing Q' or $Q^a$ group substituted with a carboxy group, an acid chloride group, an active ester group; each Q" group independently represents an alkyl group comprising 1 to 20 carbons, an aryl group comprising 1 to 20 carbons, or a foregoing Q" group substituted with a carboxy group, an acid chloride group, or an active ester group. The Q', $Q^a$ and Q" groups can further independently comprise a cycloaliphatic ring, an aromatic ring, and/or a heteroatom such as oxygen, sulfur or nitrogen. The Q', $Q^a$ or Q" groups can also together form a ring that can include a heteroatom such as oxygen, sulfur or nitrogen. In an embodiment, n is 1, one $Q^a$ group is a methyl or ethyl group, the other $Q^a$ group is a carboxylic acid, acid chloride or active ester, and all Q' and Q" groups are hydrogen.

A more specific cyclic carbonyl monomer derived from the precursor compounds of general formula (4) have the general formula (6):

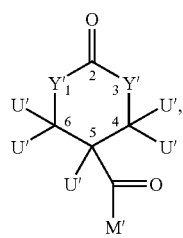

wherein each Y' independently represents O, S, NH or NU"; M' represents OH, chloride, or an active ester leaving group comprising 1 to 20 carbons; each U' group independently represents a hydrogen, a halide, an alkyl group comprising 1 to 20 carbons, a carboxy group (i.e., —COOH), a non-sugar ester group comprising 1 to 20 carbons, an amide group comprising 1 to 20 carbons, an aryl group comprising 1 to 20 carbons, or an alkoxy group comprising 1 to 20 carbons. Each U" group independently represents an alkyl group comprising 1 to 20 carbons or an aryl group comprising 1 to 20 carbons, or a foregoing U" group substituted with a non-sugar ester group or carboxy group. In an embodiment, none of the U' or U" groups comprise a non-sugar ester group or a carboxy group. In another embodiment, Y' is oxygen, M' is chloride, the U' group attached to the carbon labeled 5 is a methyl or ethyl group, and all other U' groups are hydrogen.

Isomerically pure precursor compounds of formulas (3) and (4) having a hydrogen attached to an asymmetric carbon adjacent to a non-sugar bearing ester group or carboxy group can be converted to cyclic carbonyl monomers of formula (5) and (6) without undergoing significant racemization of the asymmetric carbon. An enantiomeric excess of 80% or more, more specifically of 90%, is possible. In an embodiment, the cyclic carbonyl monomer of formula (5) or formula (6) comprises an asymmetric carbon as an (R) isomer, in an enantiomeric excess of greater than 80%, more specifically greater than 90%. In another embodiment, the cyclic carbonyl monomer of formula (5) or formula (6) comprises an asymmetric carbon as an (S) isomer, in an enantiomeric excess greater than 80%, more specifically greater than 90%.

To summarize, the cyclic carbonyl monomers of formulas (5) and (6), containing a carboxylic acid or a non-sugar ester (e.g., benzyl ester), can serve as starting materials for the preparation of cyclic carbonyl monomers containing a sugar bearing ester group. The carboxylic acid group of formulas (5) or (6) can be converted to an active carbonyl either in situ (such as with DCC) or stepwise (e.g., by way of an acid chloride, p-nitrophenyl ester, or other active ester). The active carbonyl reacts with the primary or secondary alcohol group of a protected glycoside to form the sugar bearing ester group.

Thus, a more specific cyclic carbonyl monomer derived from a compound of formula (5) contains a protected glycoside, and has the formula (7):

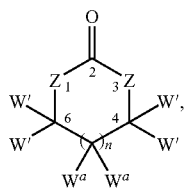

wherein at least one W' or $W^a$ group comprises a protected glycoside, each Z independently represents O, S, NH or NW"; n is an integer from 0 to 6, wherein when n is 0, carbons labeled 4 and 6 (attached to each Z group) are linked together by a single bond; and each W' and $W^a$ group independently represents a hydrogen, a halide, an alkyl group comprising 1 to 20 carbons, an ester group comprising 1 to 20 carbons, an amide group, an aryl group comprising 1 to 20 carbons, an alkoxy group comprising 1 to 20 carbons, or a foregoing W' or $W^a$ group substituted with a protected glycoside; each W''' group independently represents an alkyl group comprising 1 to 20 carbons, an aryl group comprising 1 to 20 carbons, or a foregoing W''' group substituted with a protected glycoside. The W', $W^a$ and W''' groups can further independently comprise a cycloaliphatic ring, an aromatic ring, and/or a heteroatom such as oxygen, sulfur or nitrogen. The W', $W^a$ or W''' groups can also together form a ring that can include a heteroatom such as oxygen, sulfur or nitrogen. In an embodiment, n is 1, Z is oxygen, one $W^a$ group is a methyl or ethyl group, the other $W^a$ group is a —$CO_2R$ group, where R is a protected glycoside, and all other W' and W''' groups are hydrogen.

An even more specific cyclic carbonyl monomer contains a protected glycoside bearing ester group derived from the compound of formula (6), and has the formula (8):

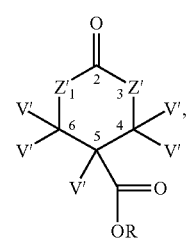

wherein each Z' independently represents O, S, NH or NV'''; R represents a protected glycoside moiety; each V' group independently represents a hydrogen, a halide, an alkyl group comprising 1 to 20 carbons, a non-sugar ester group comprising 1 to 20 carbons, an amide group comprising 1 to 20 carbons, an aryl group comprising 1 to 20 carbons, or an alkoxy group comprising 1 to 20 carbons; each V''' group independently represents an alkyl group comprising 1 to 20 carbons or an aryl group comprising 1 to 20 carbons, or a foregoing V''' group substituted with a non-sugar ester group. In an embodiment, Z' is oxygen, the V' group attached to the carbon labeled 5 is a methyl or ethyl group, and all other V' are hydrogen.

An example of a cyclic carbonyl monomer of formula (8) containing a protected glycoside bearing ester is IMFC, shown below. IMFC is prepared by reacting the cyclic carbonyl acid chloride, MTC-Cl, with 2,3;5,6-di-O-isopropylidene-D-mannofuranose, DIMF, in THF/$Et_3N$ at 40° C. for 24 hours.

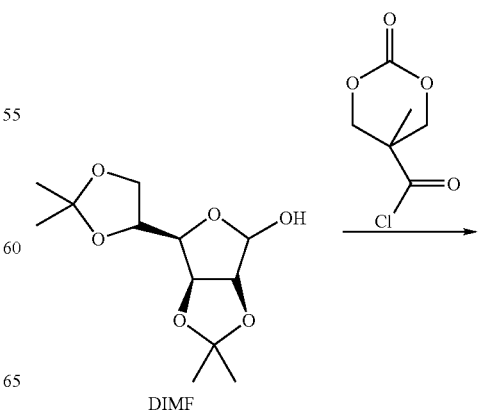

DIMF

-continued

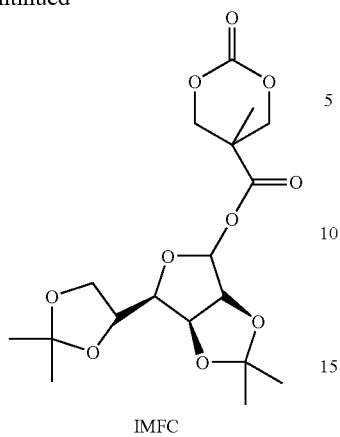

IMFC

Under similar conditions, 1,2;3,4-di-O-isopropylidene-D-galactopyranose, DIGP, reacts to form IGPC:

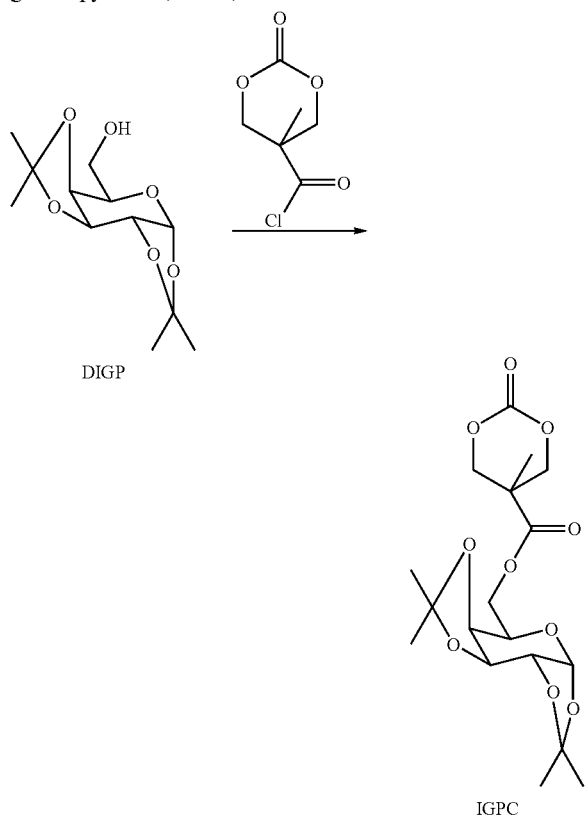

DIGP

IGPC

In another example, 1,2;5,6-di-O-isopropylidene-D-glucofuranose, DIGF, reacts to form IGFC:

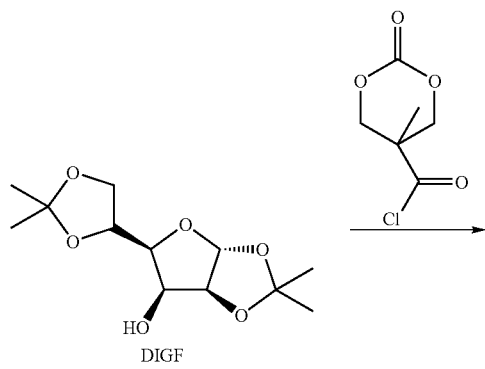

DIGF

-continued

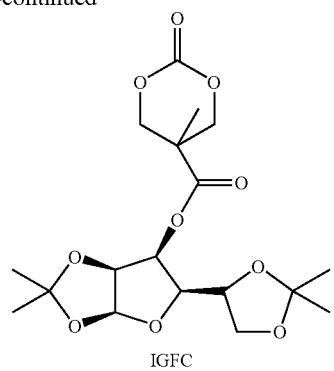

IGFC

In each of the above examples, the isomeric purity of the glycoside is preserved during ester formation.

The cyclic carbonyl monomers undergo ring-opening polymerization (ROP) to form polymers of different tacticities. Atactic, syndiotactic and isotactic forms of the polymers can be produced that depend on the cyclic monomer(s), its isomeric purity, and the polymerization conditions.

A method of ring-opening polymerization comprises forming a first mixture comprising a cyclic monomer, a catalyst, an initiator, and an optional solvent. The first mixture is then heated and agitated to effect polymerization of the cyclic monomer, forming a second mixture containing the polymer product.

Polymers prepared from the cyclic carbonyl monomers of formula (7) have the general formula (9):

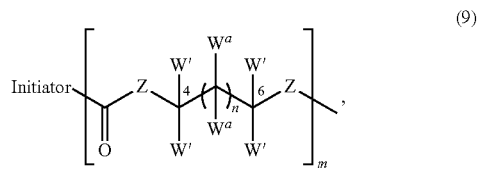

(9)

wherein at least one W' or $W^a$ group comprises a protected glycoside, m is an integer greater than 1, "Initiator" is a polymerization initiator moiety (e.g., $C_6H_5CH_2O$ derived from benzyl alcohol), each Z independently represents O, S, NH or NW'''; n is an integer from 0 to 6, wherein when n is 0, carbons labeled 4 and 6 are linked together by a single bond; and each W' and $W^a$ group independently represents a hydrogen, a halide, an alkyl group comprising 1 to 20 carbons, an ester group comprising 1 to 20 carbons, an amide group, an aryl group comprising 1 to 20 carbons, an alkoxy group comprising 1 to 20 carbons, or a foregoing W' or $W^a$ group substituted with a protected glycoside; each W''' group independently represents an alkyl group comprising 1 to 20 carbons, an aryl group comprising 1 to 20 carbons, or a foregoing W''' group substituted with a protected glycoside. More particularly, m is an integer from 1 to 10,000, from 100 to 5000, or from 100 to 1000. In an embodiment, n is 1, Z is oxygen, one $W^a$ group is a methyl or ethyl group, another $W^a$ group is a —$CO_2R$ group wherein R is a protected glycoside, and all other W' groups are hydrogen.

Treatment of the polymers with a deprotection agent produces a glycopolymer containing a unprotected glycoside moiety. By adjusting the hydrophilic/hydrophobic balance, glycopolymers can be formed that assemble into micelles. The term "unprotected glycoside," encompasses the acetal, hemi-acetal, ketal, or hemi-ketal forms, where applicable, of an unprotected glycoside moiety. In an embodiment, the glycopolymer comprises an unprotected glucose, unprotected lactose, unprotected mannose, or unprotected galactose moiety. Likewise, the terms "unprotected lactose," "unprotected mannose," "unprotected galactose," encompass the acetal, hemi-acetal, ketal or hemi-ketal forms, where applicable, of these specific unprotected glycoside units.

Polymers prepared from the cyclic carbonyl monomers of formula (8) have the general formula (10):

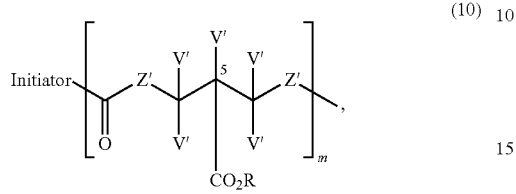

wherein R is a protected glycoside, and Z', V', "Initiator", and m have the definitions described above. In an embodiment, Z' is oxygen, V' attached to carbon labeled 5 is methyl or ethyl, all other V' groups are hydrogen, and R is a protected glycoside, more particularly a protected glucose, protected lactose, protected mannose or protected galactose. Polymers of formula (10) are also formed by ring opening polymerization, and can be deprotected to form glycopolymers. In an embodiment, the glycopolymer comprises an unprotected glucose, unprotected lactose, unprotected mannose, or unprotected galactose.

Non-limiting examples of ROP homopolymers PIMFC, PIGPC, and PIGFC, prepared from the cyclic carbonate monomers IMFC, IGPC, and IGFC, respectively, using benzyl alcohol initiator, are shown in the following structures, where m has the meaning described above:

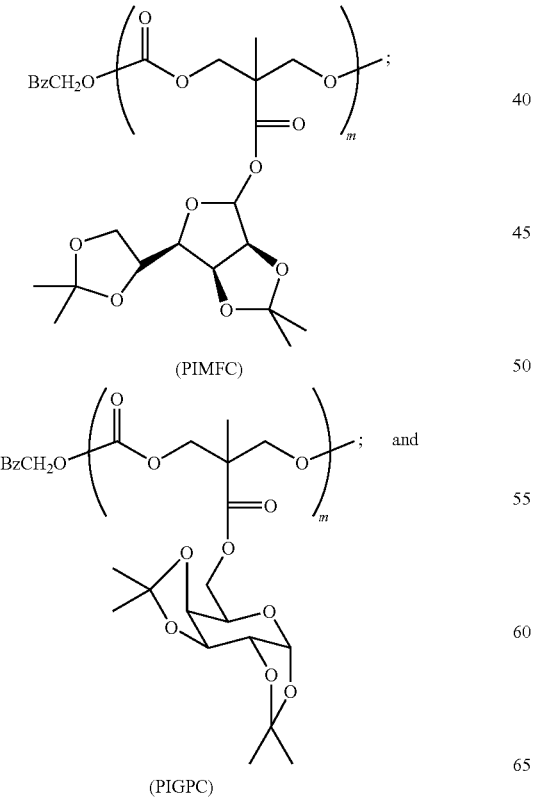

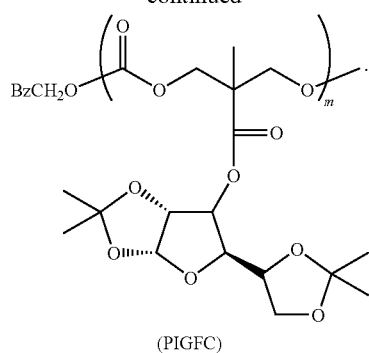

Non-limiting examples of glycopolymers derived from the homopolymers PIGPC, PIGFC, PIMFC, PICXF by removal of the acetonide protecting groups, are shown in the following structures u-PIGPC, u-PIGFC, u-PIMFC, u-PICXF, where the "u" in the name designates unprotected, and m has the meaning described above:

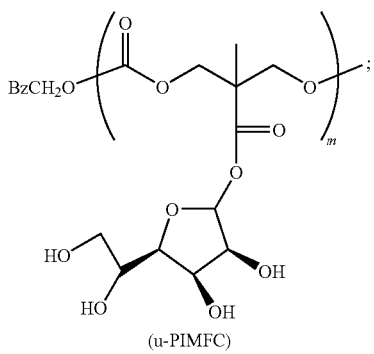

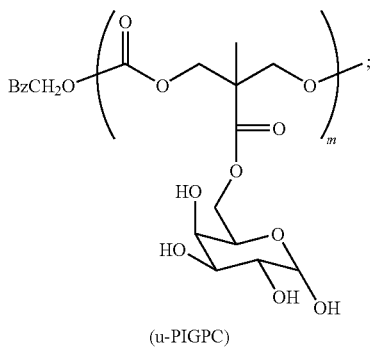

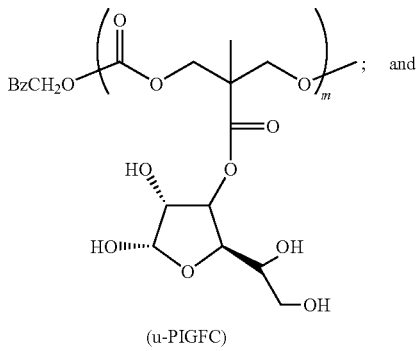

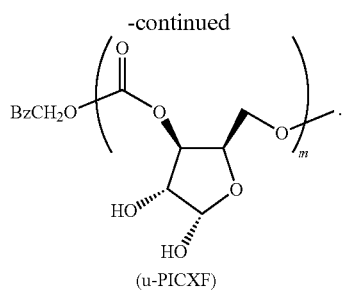

(u-PICXF)

Random ROP copolymers can be prepared using a mixture comprising one or more of cyclic carbonyl monomers, wherein at least one cyclic carbonyl monomer comprises a protected glycoside. As before, post-polymerization deprotection of the protected glycoside provides a glyco-copolymer. In an embodiment, the cyclic carbonyl monomer is selected from the group consisting of IGPC, IMFC, TMC, IGFC and combinations thereof In a related method, n cyclic carbonyl monomers, wherein one or more of the cyclic carbonyl monomers comprises a protected glycoside, are sequentially polymerized by ring opening polymerization to form an n-block copolymer, where n is 1 to 10. The block copolymers can comprise one or more blocks per cyclic carbonyl monomer. Many configurations of block sequences are possible. For example, diblock copolymers comprising A and B blocks can be represented as -AB-copolymers. Triblock copolymers comprising A and B blocks can be represented as -ABA- or -BAB-copolymers. Tetrablock copolymers comprising A and B blocks can be represented as -ABAB-copolymers. Triblock polymers comprising A, B, and C blocks can be represented, for example, as -ABC-, -ACB-, or -BAC-copolymers. Tetrablock copolymers comprising A, B and C blocks can be represented, for example, as -ABCA-, -ABCB, -ACAB, -BCAB-, -BCAC-, -CABA, and -CABC-copolymers. The above examples of block sequences in block copolymers are not meant to be limiting.

The ring opening polymerization is generally conducted in a reactor under inert atmosphere such as nitrogen or argon. The polymerization can be performed by solution polymerization in an inactive solvent such as benzene, toluene, xylene, cyclohexane, n-hexane, dioxane, chloroform and dichloroethane, or by bulk polymerization. The ROP reaction temperature can be from 20° to 250° C. Generally, the reaction mixture is heated at atmospheric pressure for 0.5 to 72 hours to effect polymerization. Subsequently, additional cyclic monomer and catalyst can be added to the second mixture to effect block polymerization if desired.

Exemplary ROP catalysts include tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; tertiary amines such as triallylamine, triethylamine, tri-n-octylamine and benzyldimethylamine; heteropolyacids such as phosphotungstic acid, phosphomolybdic acid, silicotungstic acid and alkali metal salt thereof, zirconium compounds such as zirconium acid chloride, zirconium octanoate, zirconium stearate and zirconium nitrate. More particularly, the catalyst is zirconium octanoate, tetraalkoxy zirconium or a trialkoxy aluminum compound.

Other ROP catalysts include metal-free organocatalysts that can provide a platform to polymers having controlled, predictable molecular weights and narrow polydispersities. Examples of organocatalysts for the ROP of cyclic esters, carbonates and siloxanes are 4-dimethylaminopyridine, phosphines' N-heterocyclic carbenes (NHC), bifunctional aminothioureas, phosphazenes, amidines, and guanidines.

The ROP reaction mixture comprises at least one catalyst and, when appropriate, several catalysts together. The ROP catalyst is added in a proportion of 1/20 to 1/40,000 moles relative to the cyclic monomers, and preferably of 1/1,000 to 1/20,000 moles. In an embodiment, the catalyst is a combination of 1,8-diazabicyclo[5.4.0]undec-7-ene (DBU), and 1-(3,5-bis(trifluoromethyl)phenyl-3-cyclohexyl-2-thiourea, TU.

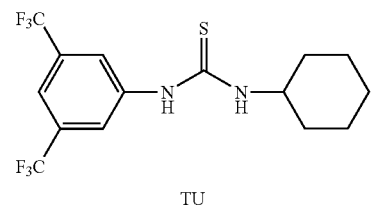

TU

The ROP reaction mixture also comprises an initiator. Initiators generally include nucleophiles such as alcohols, amines or thiols. The initiator can be monofunctional, difunctional or multifunctional such as dendritic, polymeric or related architectures. Monofunctional initiators can include nucleophiles with protected functional groups that include thiols, amines, acids and alcohols. A typical initiator is phenol or benzyl alcohol.

Well-known apparatuses can be used for performing the ROP polymerization. An example of a tower type reaction apparatus includes a reaction vessel comprising helical ribbon wings and transformational spiral baffles. Examples of sideways type reaction apparatuses include sideways type one-or twin-shaft kneaders comprising agitation shafts that have a row of transformational wings arranged in parallel to each other. In addition, the reaction apparatus can be either a batch type or a continuous one.

The ROP product can be a homopolymer, copolymer, or block copolymer. The biodegradable polymer can have a number-average molecular weight of usually 1,000 to 200,000, more particularly 2,000 to 100,000, and still more particularly 5,000 to 80,000.

The polymers disclosed herein can assemble into micelles, and are therefore of interest as a means for drug transport and release, and protein-binding interactions. The polymer products can also be applied to conventional molding methods such as compression molding, extrusion molding, injection molding, hollow molding and vacuum molding, and can be converted to molded articles such as various parts, receptacles, materials, tools, films, sheets and fibers. A molding composition can be prepared comprising the polymer and various additives, including for example nucleating agents, pigments, dyes, heat-resisting agents, antioxidants, weather-resisting agents, lubricants, antistatic agents, stabilizers, fillers, strengthened materials, fire retardants, plasticizers, and other polymers. Generally, the molding compositions comprise 30 wt. % to 100 wt. % or more of the polymer based on total weight of the molding composition. More particularly, the molding composition comprises 50 wt. % to 100 wt. % of the polymer. The polymers, and articles molded therefrom, can be biodegradable.

The polymer product of the ROP polymerization can be formed into free-standing or supported films by known methods. Non-limiting methods to form supported films include dip coating, spin coating, spray coating, and doctor blading. Generally, such coating compositions comprise 0.01 wt. % to 90 wt. % of the polymer based on total weight of the coating composition. More particularly, the molding composition comprises 1 wt. % to 50 wt. % of the polymer based on total weight of the coating composition. The coating compositions generally also include a suitable solvent necessary to dissolve the polymer product.

The coating compositions can further include other additives selected so as to optimize desirable properties, such as optical, mechanical, and/or aging properties of the films. Non-limiting examples of additives include surfactants, ultraviolet light absorbing dyes, heat stabilizers, visible light absorbing dyes, quenchers, particulate fillers, and flame retardants. Combinations of additives can also be employed.

The following examples demonstrate the preparation of cyclic carbonyl monomers comprising sugar moieties, and the polymerization of the monomers to form homopolymers and block copolymers.

EXAMPLES

Materials.

Reagents were commercially available from Aldrich and used without any other purification unless otherwise noted.

5-Methyl-5-carboxyl-1,3-dioxan-2-one (MTC-OH) was synthesized from bis-MPA according to Scheme 1, as reported by R. C. Pratt, F. Nederberg, R. M. Waymouth, J. L. Hedrick, *Chem. Commun.*, 2008, 1, 114.

1-(3,5-Bis(trifluoromethyl)phenyl-3-cyclohexyl-2-thiourea (TU) was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, *Macromolecules*, 2006, 39 (23), 7863-7871, and dried by stirring in dry THF over $CaH_2$, filtering, and removing solvent under vacuum. 1,8-Diazabicyclo[5.4.0]undec-7-ene (DBU; 98%) and benzyl alcohol were stirred over $CaH_2$, vacuum distilled, then stored over molecular sieves (3 Å).

Test Methods.

Melting points of monomers were recorded with a capillary tube melting point apparatus and were uncorrected. $^1$H— and $^{13}$C-NMR spectra were obtained on a Bruker Avance 400 instrument operated at 400 MHz, using $CDCl_3$ solutions unless otherwise noted. Gel permeation chromatography (GPC) was performed in THF at 30° C. using a Waters chromatograph equipped with four 5 micrometer Waters columns (300 mm×7.7 mm) connected in series with increasing pore size (10, 100, 1000, $10^5$, $10^6$ angstroms), a Waters differential refractometer for refractive index (RI) detection and a 966 photodiode array detector, and calibrated with polystyrene standards (750–(2×$10^6$) g.mol$^{-1}$)

Example 1

Synthesis of IGFC

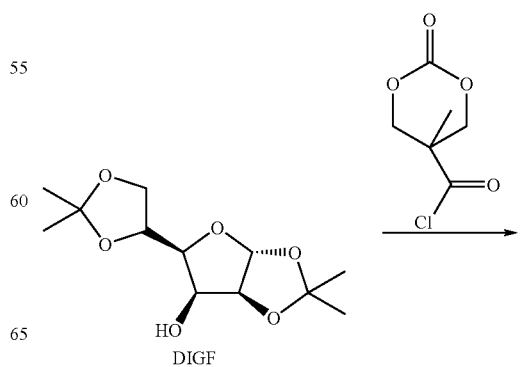

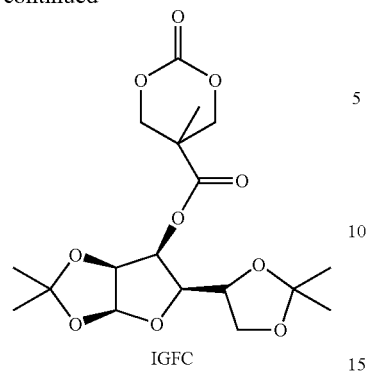

IGFC

MCT-OH (2.0 g; 12.5 mmol) was dissolved in dry THF (30 ml) with 3 drops of DMF. A solution of oxalyl chloride (1.75 g; 13.8 mmol) in dry THF (12 ml) was added and the mixture was allowed to react one more hour under stirring and nitrogen flow. Volatiles were then removed under vacuum and $^1$H-NMR analysis evidenced a complete conversion of the acid chloride. The acid chloride was redissolved in THF (30 ml) and a solution of 1,2;5,6-di-O-isopropylidene-D-glucofuranose (DIGF) (3.0 g; 11.5 mmol) and dried triethylamine (1.51 g; 15 mmol) in THF was added, causing the formation of a white precipitate. The mixture was stirred at 40° C. for 48 hours before filtration of the triethylamine salt and concentration of the crude product under reduced pressure. The product was purified by recrystallization in diethyl ether to give a white solid, m.p. 132° C. to 134° C. Yield=1.62 g (50%). $^1$H-NMR: δ 5.92 (d, J=3.6 Hz, 1H, H-a), 5.40 (d, J=2.9 Hz, 1H, H-c), 4.71 (m, 2H, H-j), 4.47 (d, J=3.6 Hz, 1H, H-b), 4.26-4.12 (m, 5H, H-d+H-e+H-f+H-j'), 4.01 (m, 1H, H-g), 1.54-1.32 (5 s, 15H, H-h+H-i). $^{13}$C-NMR: δ 181.5, 171.2, 147.1, 113.1, 110.0, 105.4, 83.6, 80.5, 73.4, 73.2, 72.8, 68.3, 27.1, 27.0, 26.6, 25.5, 17.8.

Example 2

Synthesis of IMFC

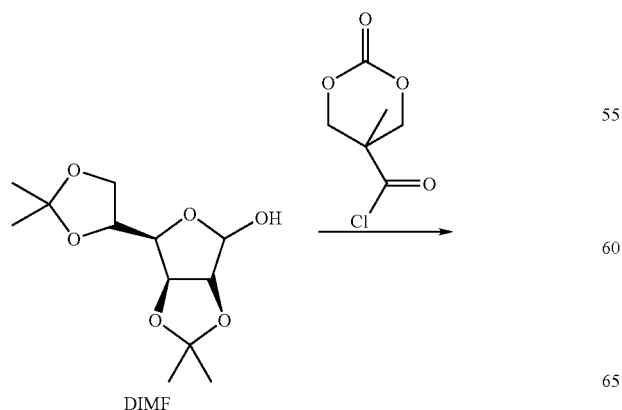

DIMF

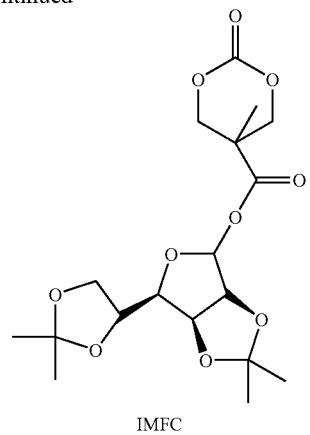

IMFC

IMFC was synthesized according to the same procedure used for IGFC, using 2,3;5,6-Di-O-isopropylidene-D-mannofuranose (DIMF) as the coupling alcohol (3.0 g; 11.5 mmol). The product was purified by recrystallization in diethyl ether to give a yellowish solid, mp 142-144° C. Yield=2.55 g (55%). $^1$H-NMR: δ 6.22 (s, 1H, H-a), 4.89 (dd, $J_1$=5.8 Hz, $J_2$=3.5 Hz, 1H, H-b), 4.72 (d, J=5.8 Hz, 2H, H-d), 4.66 (m, 2H, H-j), 4.41 (m, 1H, H-c), 4.22 (m, 2H, H-j'), 4.11 (dd, $J_1$=8.8 Hz, $J_2$=2.4 Hz, 2H, H-e), 4.03 (m, 2H, Hf+H-g), 1.50-1.33 (5 s, 15H, H-h+H-i). $^{13}$C-NMR: δ 170.1, 147.2, 114.0, 109.9, 103.0, 85.3, 83.5, 79.5, 73.3, 73.1, 67.2, 40.8, 27.3, 26.3, 25.5, 25.0, 17.6.

Example 3

Synthesis of IGPC

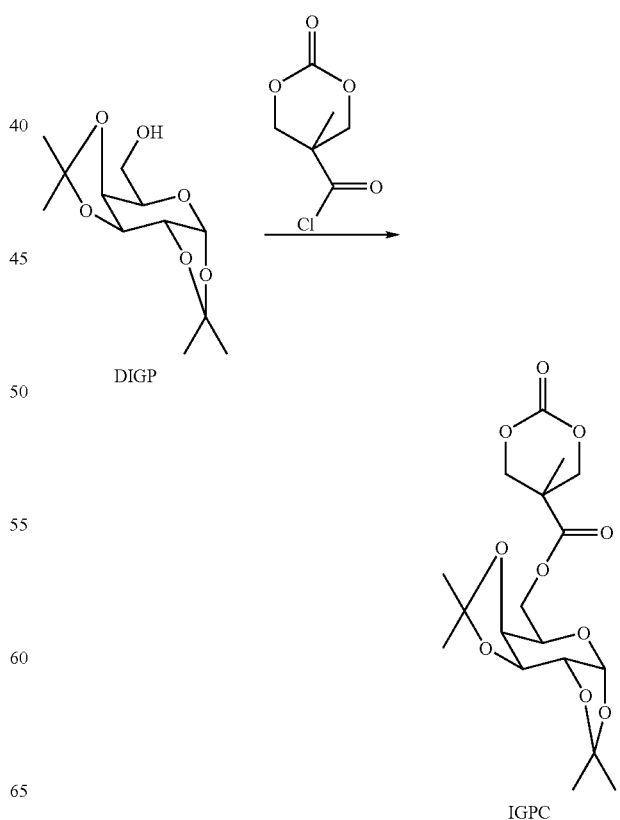

IGPC was synthesized according to the same procedure used for IGFC, using 1,2;3,4-Di-O-isopropylidene-D-galactopyranose (DIGP) as the coupling alcohol (3.0 g; 11.5 mmol) and purified by column chromatography (silica, 2:1 ethyl acetate/hexanes) leading to the desired product as an oil that slowly crystallized as a white solid, m.p. 117° C. to 120° C. Yield=2.36 g (51%). $^1$H-NMR: δ 5.54 (d, J=5.3 Hz, 1H, H-a), 4.73 (m, 2H, H-h), 4.64 (dd, $J_1$=8.0 Hz, $J_2$=2.7 Hz, 1H, H-c), 4.44 (dd, $J_1$=11.7 Hz, $J_2$=3.9 Hz, 1H, H-b), 4.35 (m, 2H, H-f+H-f'), 4.22 (m, 3H, H-h'+H-d), 4.04 (ddd, $J_1$=8.8 Hz, $J_2$=3.9 Hz, 1H, H-e), 1.51-1.35 (5 s, 15H, H-g+H-i). $^{13}$C-NMR: δ 173.3, 147.2, 110.2, 109.2, 96.6, 73.3, 71.2, 71.1, 70.8, 66.2, 65.2, 40.5, 26.3, 25.3, 24.8, 18.2.

Example 4

Synthesis of 1,2-O-isopropylidene-3,5-O-dioxan-6-one-D-xylofuranose (ICXF)

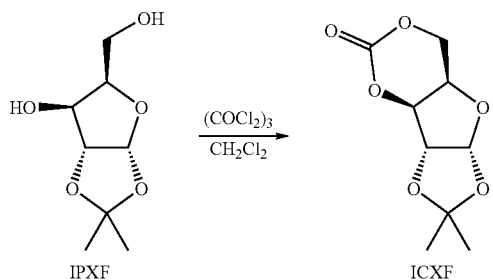

1,2-O-isopropylidene-D-xylofuranose (IPXF) (5.0 g, 26.3 mmol) was dissolved in 80 ml of $CH_2Cl_2$ and pyridine (13 ml, 0.16 mol) and the solution was chilled at −78° C. under $N_2$. A solution of triphosgene (3.9 g, 13.1 mmol) in $CH_2Cl_2$ was added dropwise under stirring. The addition completed, the mixture was allowed to warm up to room temperature for 2 hours. The reaction was quenched by addition of saturated aqueous $NH_4Cl$ (40 ml), after which the organic layer was successively washed with 1 M aqueous HCl (3×50 ml) and saturated $NaHCO_3$ (1×50 ml), then dried over $MgSO_4$, filtered and concentrated under vacuum. The crude product was recrystallized in toluene to give a yellowish crystalline solid. Yield: 3.0 g (53%). Characterization matched the literature. Polymerizations.

The ROP of the sugar-based monomers was performed using the superbasic amidine 1,8-diazabicyclo[5,4,0]undec-7-ene (DBU) catalyst with a thiourea TU co-catalyst, initiated by benzyl alcohol.

Example 5

Homopolymerization of IGPC

IGPC (100 mg, 0.25 mmol), TU (4.5 mg, 0.013 mmol) and DBU (1.9 mg, 0.013 mmol) were mixed together in a vial. 0.25 ml of a solution of benzyl alcohol (0.02 M) in dichloromethane was added and the mixture was stirred at room temperature during 3 hours. An aliquot was taken and quenched with benzoic acid as well as the remaining polymer solution. The aliquot was dried and analyzed by NMR for conversion data. The remaining solution was precipitated in methanol, filtered and dried overnight at 40° C.

Examples 6-8

IMFC, IGFC, and ICXF were homopolymerized (Examples 6-8 respectively) under similar conditions used for IGPC. High conversion of monomer to polymer was achieved within 3 hours at room temperature, as shown in Table 1 further below.

Polymerization of ICXF was already reported using organometallic catalysts (MAO, IBAO, Sn(Oct)2, Al(OiPr)3). The homopolymerization herein was accomplished using a metal free catalyst/cocatalyst combination DBU/TU in methylene chloride to achieve high monomer-to-polymer conversions within 16 hours. Narrowly dispersed polymers with molecular weights that followed the monomer-to-initiator initial ratio were obtained (Table 1).

TABLE 1

| Example | Monomer | Conv.[a] (%) | Time (hours) | Targeted $M_n$ (g·mol$^{-1}$) | Reached $M_n$[a] (g·mol$^{-1}$) | PDI[b] |
|---|---|---|---|---|---|---|
| 5 | IGPC | 93 | 3 | 20,200 | 17,000 | 1.20 |
| 6 | IMFC | 93 | 3 | 20,200 | 17,800 | 1.27 |
| 7 | IGFC | 86 | 3 | 20,200 | 19,000 | 1.28 |
| 8 | ICXF | 83 | 16 | 10,900 | 8900 | 1.25 |

[a]As obtained by $^1$H-NMR.
[b]As obtained by GPC versus polystyrene standards.

The molecular weights, determined by 1H-NMR spectroscopy, comparing anomeric proton in repetitive units (5.50 ppm for IGPC, 5.87 ppm for IGFC, and 6.15 ppm for IMFC) with methylene protons in the initiating benzyl alcohol (5.19 ppm), showed good correlation between targeted molecular weights and those obtained experimentally. Moreover, narrow polydispersities and monomodal molecular weight distributions were obtained. These combined data demonstrate the efficacy of polymerization using organocatalytic ROP yielding narrowly dispersed polymers of predictable molecular weights. Although a number of cyclic carbonate monomers have been synthesized and polymerized in the past by more conventional anionic and organometallic ROP methods, excessively bulky substituents (e.g., 2,2-diphenyl) proved to render ring-opening of the carbonate thermodynamically unfavorable.

Interestingly, for monomers IGPC, IMFC, and IGFC, substitution at the 5-position does not seem to interfere sterically with the polymerization reaction. The polymerization proceeded to high conversion, although the rate was significantly slower.

General Procedure for Preparing Block Copolymers.

Block copolymers were prepared according to Scheme 2:

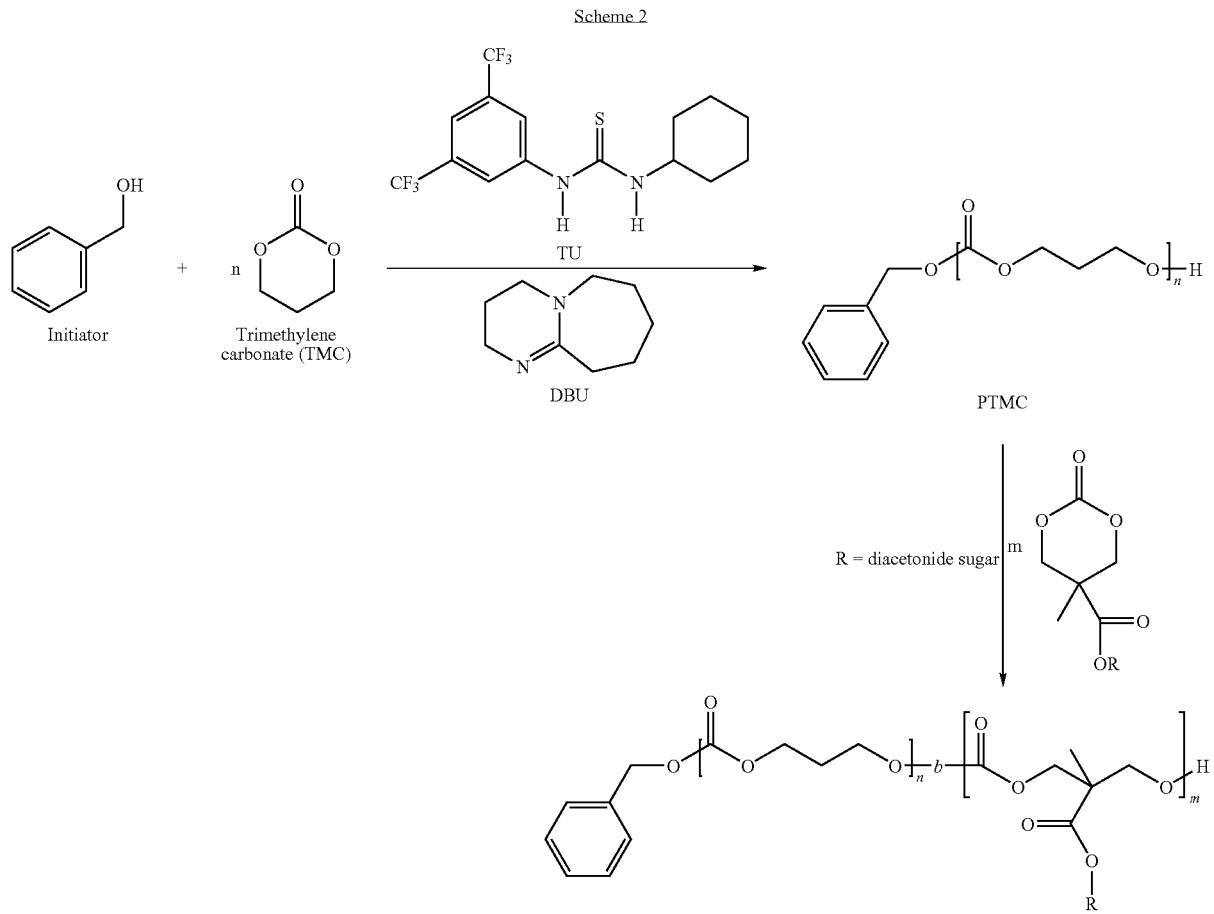

The polymerizations were performed in a one-pot, two step process using a sequential polymerization approach. A first block, poly(trimethylene carbonate) (PTMC), was synthesized to near quantitative conversion (98%, Mn=5000g.mol-1, PDI=1.1), followed by the addition of a second monomer (IGPC, IMFC, and IGFC) to the reaction mixture for the growth of the second block. The synthesis and chain extension of the copolymers was monitored by 1H-NMR and GPC. In Scheme 2, the diacetonide sugar, R, is the protected glycoside moiety.

Table 2, further below, summarizes the results of block copolymers formed, and shows that exceptional control was achieved for each of the block copolymers.

Example 9-11

Block Copolymerizations of Trimethylene Carbonate (TMC) and IGPC

Trimethylene carbonate (100 mg, 1 mmol), TU (17.5 mg, 0.05 mmol) and DBU (7.5 mg, 0.05 mmol) were mixed together in a vial. 0.5 ml of a solution of benzyl alcohol (0.04 M) in dichloromethane was added and the mixture was stirred at room temperature during 3 hours to form poly(trimethylene carbonate) (PTMC). An aliquot was taken and quenched with benzoic acid, dried and redissolved in $CDCl_3$ for first block conversion calculation. IGPC (200 mg, 0.5 mmol) was added to the polymer mixture for chain extension during 90 min. An aliquot was again taken for conversion data and the remaining solution was quenched with benzoic acid, precipitated in methanol, filtered and dried overnight at 40° C. Three polymerizations were conducted having a targeted Mn of 10,400, 15,300, and 25,300. The results are shown in Table 2. The GPC chromatogram, FIG. 1, showed the expected increase in molecular weight after the addition of the second monomer, as evidenced by a shift of the polymer trace to shorter elution time. FIG. 1 compares GPC chromatograms for the block copolymer formed from TMC and IGPC, designated PTMC-b-PIGPC, with poly(trimethylene carbonate) (PTMC) homopolymer.

Examples 12-14

The Procedure Used in Examples 9-11 was Repeated, Replacing IGPC with IMFC

Examples 15-17

The Procedure Used in Examples 9-11 was Repeated, Replacing IGPC with IGFC

TABLE 2

| Example | Monomer | Conv. sugar monomer[a] (%) | Targeted $M_n$ (g · mol$^{-1}$) | Reached $M_n$[a] (g · mol$^{-1}$) | PDI[b] |
|---|---|---|---|---|---|
| 9 | IGPC | 88 | 10,400 | 9300 | 1.24 |
| 10 | IGPC | 92 | 15,300 | 14,200 | 1.26 |

TABLE 2-continued

| Example | Monomer | Conv. sugar monomer[a] (%) | Targeted $M_n$ (g·mol$^{-1}$) | Reached $M_n$[a] (g·mol$^{-1}$) | PDI[b] |
|---|---|---|---|---|---|
| 11 | IGPC | 93 | 25,300 | 25,000 | 1.25 |
| 12 | IMFC | 87 | 10,400 | 8400 | 1.25 |
| 13 | IMFC | 90 | 15,300 | 12,700 | 1.25 |
| 14 | IMFC | 91 | 25,300 | 26,200 | 1.26 |
| 15 | IGFC | 75 | 10,400 | 9100 | 1.22 |
| 16 | IGFC | 94 | 15,300 | 13,200 | 1.23 |
| 17 | IGFC | 94 | 25,300 | 22,900 | 1.25 |

[a]As obtained by 1H-NMR.
[b]As obtained by GPC vs. polystyrene standards.
Conditions: (a: PTMC block formation) 1 M in TMC, 0.02 M BzOH, 0.05 M DBU, 0.05 M TU, CH$_2$Cl$_2$, R.T., 3 hours (b: Chain extension) 0.25-1 M in monomer, 0.05 M DBU, 0.05 M TU, CH$_2$Cl$_2$, R.T., 90 min.

Example 18

Selective Hydrolysis of Isopropylidene Protecting Group

Once the homopolymers and block copolymers were prepared, the acetonide protecting groups along the glycopolymer chains could be selectively removed with aqueous formic acid solution to regenerate hydroxyl groups. 1H-NMR showed an upfield shift of sugar chemicals shifts along with the disappearance of the isopropylidene groups, while SEC exhibited narrow monomodal distributions, attesting of selective hydrolysis reaction of the acetonide protecting groups. Polymers varying in composition were targeted in order to tune the hydrophilic/hydrophobic balance. The unprotected glycoside moieties in the homopolymers and block copolymers had the structure of the corresponding unprotected glycoside in the structures u-PIGPC, u-PIMFC, and u-PIGFC described above.

Figure 2:
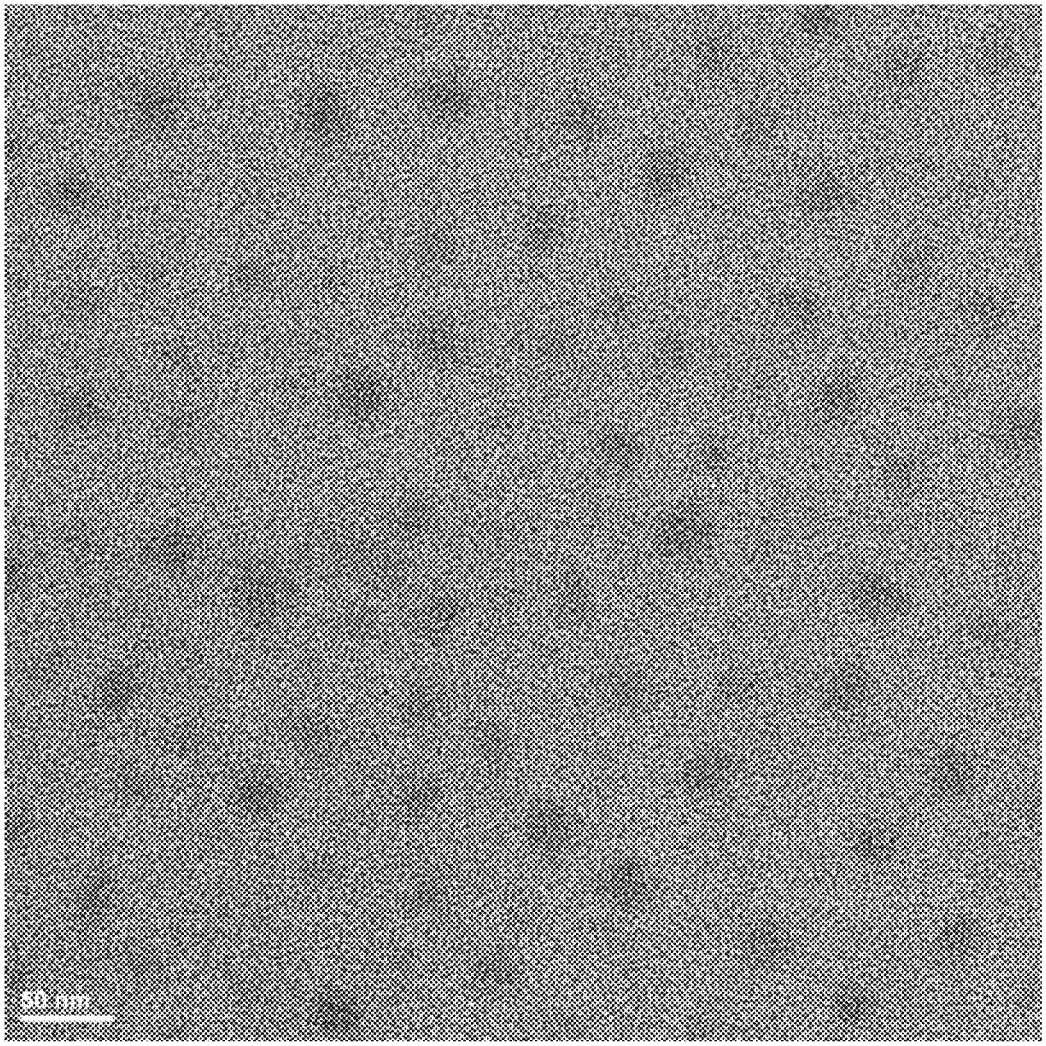
FIG. 2 is a transmission electron micrograph (TEM) showing spherical micelles of average diameter 20-30 nm after selective deprotection of a galactose polymer.

The protected polymer (0.25 g) was dissolved in 2.5 ml of a 4:1 formic acid aqueous solution during 48 hours. Dialysis against water using 3.5K cutoff membrane was performed during 48 hours changing water every 6 hours. The micellar solution (FIG. 2), having spherical micelles of average diameter 20-30 nanometers, was then transferred in a vial and freeze-dried to give a white powder in good yields (90%). $^1$H NMR spectra were recorded in DMSO-d$_6$.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one ore more other features, integers, steps, operations, element components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A cyclic carbonyl monomer of the formula (7):

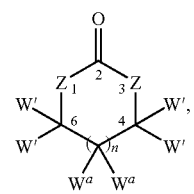

(7)

wherein at least one W' or W$^a$ group comprises a protected glycoside; each Z independently represents O, S, NH or NW'''; n is an integer from 0 to 6 wherein when n is 0, carbons labeled 4 and 6 are linked together by a single bond; each W' and W$^a$ group independently represents a hydrogen, a halide, an alkyl group comprising 1 to 20 carbons, an ester group comprising 1 to 20 carbons, an amide group, an aryl group comprising 1 to 20 carbons, an alkoxy group comprising 1 to 20 carbons, or a foregoing W' or W$^a$ group substituted with a protected glycoside; and each W''' group independently represents an alkyl group comprising 1 to 20 carbons, an aryl group comprising 1 to 20 carbons, or a foregoing W''' group substituted with a protected glycoside.

2. The cyclic carbonyl monomer of claim 1, wherein the protected glycoside is a protected glucose, protected lactose, protected mannose, or a protected galactose.

3. The cyclic carbonyl monomer of claim 1, wherein the protected glycoside comprises an acetonide protecting group.

4. The cyclic carbonyl monomer of claim 1, wherein Z is oxygen, n is one, one W$^a$ group in formula (7) is a methyl or ethyl group, another W$^a$ group is a —CO$_2$R group, wherein R is a protected glycoside, and W' and W''' groups are each hydrogen.

5. The cyclic carbonyl monomer of claim 1, wherein the cyclic carbonyl monomer is selected from the group consisting of:

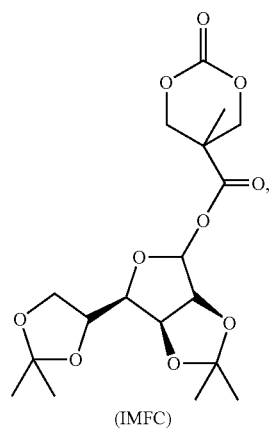

(IMFC)

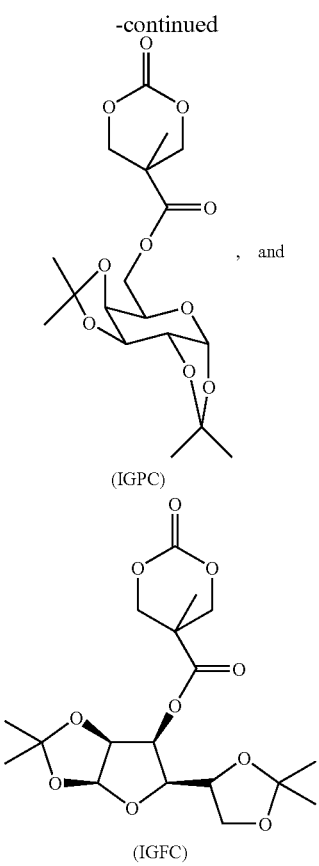

(IGPC)

(IGFC)

6. A method of preparing a cyclic carbonyl monomer comprising a protected glycoside, comprising:
preparing a first cyclic carbonyl monomer comprising a reactive carboxyl group selected from the group consisting of free carboxylic acid, acid chloride, and active ester; and
esterifying the reactive carboxyl group of the first cyclic carbonyl monomer with a free hydroxyl group of a protected glycoside to produce the cyclic carbonyl monomer comprising the protected glycoside.

7. The method of claim 6, wherein the first cyclic carbonyl monomer has the general formula (5):

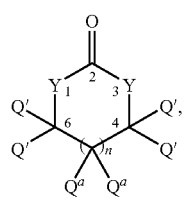

(5)

wherein at least one Q' or $Q^a$ group comprises a reactive carboxyl group selected the group consisting of carboxylic acid, acid chloride or active ester; each Y independently represents O, S, NH or NQ"; n is an integer from 0 to 6, wherein when n is 0, carbons labeled 4 and 6 are linked together by a single bond; each Q' and $Q^a$ group independently represents a hydrogen, a halide, a carboxy group, an acid chloride group, an active ester, an alkyl group comprising 1 to 20 carbons, a non-active ester group comprising 1 to 20 carbons, an amide group, an aryl group comprising 1 to 20 carbons, an alkoxy group comprising 1 to 20 carbons, or a foregoing Q' or $Q^a$ group substituted with a carboxy group, an acid chloride group, an active ester group; and each Q" group independently represents an alkyl group comprising 1 to 20 carbons, an aryl group comprising 1 to 20 carbons, or a foregoing Q" group substituted with a carboxy group, an acid chloride group, or an active ester group.

8. The method of claim 7, wherein Y is oxygen, n is 1, one $Q^a$ group is a methyl or ethyl group, another $Q^a$ group is a carboxylic acid, acid chloride or active ester, and all other Q' and Q" groups are hydrogen.

9. The method of claim 6, wherein the first cyclic carbonyl monomer is MTC-Cl, prepared by treating MTC-OH with oxalyl chloride.

10. The method of claim 6, wherein the protected glycoside is a protected glucose, protected lactose, protected mannose, or a protected galactose.

11. The method of claim 6, wherein the protected glycoside comprises an acetonide protecting group.

12. The method of claim 6, wherein the first cyclic carbonyl monomer has the general formula (6):

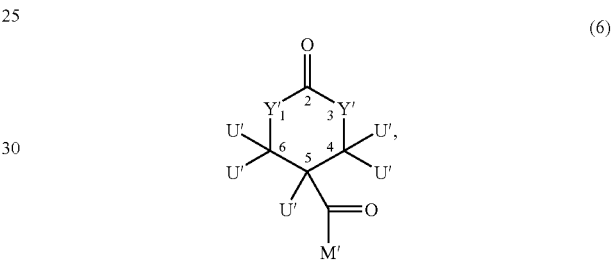

(6)

wherein each Y' independently represents O, S, NH or NU"; M' represents OH, Cl, or an active ester leaving group comprising 1 to 20 carbons; each U' group independently represents a hydrogen, a halide, an alkyl group comprising 1 to 20 carbons, a carboxy group, a non-sugar ester group comprising 1 to 20 carbons, an amide group comprising 1 to 20 carbons, an aryl group comprising 1 to 20 carbons, or an alkoxy group comprising 1 to 20 carbons; and each U" group independently represents an alkyl group comprising 1 to 20 carbons or an aryl group comprising 1 to 20 carbons, or a foregoing U" group substituted with a non-sugar ester group or a carboxy group.

13. The method of claim 7, wherein Y' is oxygen, M' is chloride, the U' group attached to the carbon labeled 5 is a methyl or ethyl group, and all other U' groups are hydrogen.

14. A polymer of formula (9)

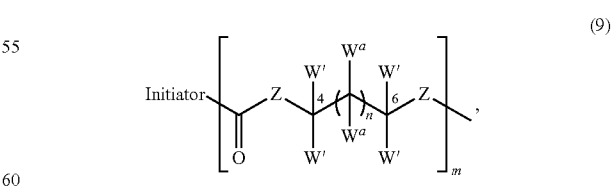

(9)

wherein at least one W' or $W^a$ group comprises a protected glycoside; m is an integer greater than 1; "Initiator" is a polymerization initiator moiety; each Z independently represents O, S, NH or NW"; n is an integer from 0 to 6, wherein when n is 0, carbons labeled 4 and 6 are linked together by a single bond; and each W' and $W^a$ group independently represents a hydrogen, a halide, an alkyl group comprising 1 to 20 carbons, an ester group comprising 1 to 20 carbons, an amide group, an aryl group comprising 1 to 20 carbons, an alkoxy group comprising 1 to 20 carbons, or a foregoing W' or $W^a$ group substituted with a protected glycoside; and each W" group independently represents an alkyl group comprising 1 to 20 carbons, an aryl group comprising 1 to 20 carbons, or a foregoing W" group substituted with a protected glycoside.

15. The polymer of claim 14, wherein n is 1, Z is oxygen, one $W^a$ group is a methyl or ethyl group, another $W^a$ group is a —$CO_2R$ group wherein R is a protected glycoside, and all other W' groups are hydrogen.

16. The polymer of claim 14, wherein at least one W' or $W^a$ group comprises an unprotected glycoside; m is an integer greater than 1; "Initiator" is a polymerization initiator moiety; each Z independently represents O, S, NH or NW"; n is an integer from 0 to 6, wherein when n is 0, carbons labeled 4 and 6 are linked together by a single bond; and each W' and $W^a$ group independently represents a hydrogen, a halide, an alkyl group comprising 1 to 20 carbons, an ester group comprising 1 to 20 carbons, an amide group, an aryl group comprising 1 to 20 carbons, an alkoxy group comprising 1 to 20 carbons, or a foregoing W' or $W^a$ group substituted with an unprotected glycoside; and each W" group independently represents an alkyl group comprising 1 to 20 carbons, an aryl group comprising 1 to 20 carbons, or a foregoing W" group substituted with an unprotected glycoside; and wherein the unprotected glycoside is an unprotected glucose, unprotected lactose, unprotected mannose, or unprotected galactose.

17. A method of ring opening polymerization comprising:
forming a reaction mixture comprising a cyclic carbonyl monomer comprising a protected glycoside, a catalyst, an initiator, and an optional solvent; and
heating the reaction mixture to form a polymer comprising a protected glycoside.

18. The method of claim 17, wherein the cyclic carbonyl monomer is selected from the group consisting of IGPC, IMFC, TMC, IGFC and combinations thereof 19. The method of claim 17, wherein the catalyst is a metal free organic catalyst.

20. The method of claim 17, further comprising treating the polymer with a deprotection agent to produce a glycopolymer.

* * * * *